United States Patent [19]

Zeevi et al.

[11] Patent Number: 5,782,853
[45] Date of Patent: Jul. 21, 1998

[54] SURGICAL HANDLE FOR SURGICAL BLADES AND PUNCHES

[76] Inventors: Eli I. Zeevi, 2095 California St., Suite 506, San Francisco, Calif. 94109; Douglas B. Dority, 25 Castlerock Dr., Mill Valley, Calif. 94941

[21] Appl. No.: 772,266

[22] Filed: Dec. 23, 1996

Related U.S. Application Data

[63] Continuation-in-part of Ser. No. 713,407, Sep. 13, 1996.

[51] Int. Cl.[6] ............................................. A61B 17/34
[52] U.S. Cl. ................................... 606/187; 30/329
[58] Field of Search ............................. 606/187, 184, 606/185, 167, 170; 30/329, 330

[56] References Cited

U.S. PATENT DOCUMENTS

| | | |
|---|---|---|
| 3,521,686 | 7/1970 | Weinmann et al. |
| 3,934,591 | 1/1976 | Gleason |
| 4,029,319 | 6/1977 | Christen |
| 4,400,878 | 8/1983 | Vaudreuil |
| 4,410,184 | 10/1983 | Anderson |
| 4,817,284 | 4/1989 | Sacherman et al. |
| 5,175,934 | 1/1993 | Chao |

Primary Examiner—Michael Buiz
Assistant Examiner—Kevin Truong
Attorney, Agent, or Firm—Burns, Doane, Swecker, & Mathis, L.L.P.

[57] ABSTRACT

A surgical handle according to the present invention accommodates a plurality of surgical implements used in hair transplantation procedures. In particular, the surgical handle accommodates both surgical mini-blades having a generally flat shape and surgical punches having a generally cylindrical shape. The handle includes a chucking mechanism for removably receiving different shaped surgical implements. The chucking mechanism includes an elongated lengthwise slot for receiving the mini-blades and a cylindrical central bore for receiving cylindrical surgical implements. The handle according to the present invention avoids the necessity of having different handles to accommodate different implements which are used in a single hair transplantation procedure.

6 Claims, 3 Drawing Sheets

SURGICAL HANDLE FOR SURGICAL BLADES AND PUNCHES

CROSS REFERENCE TO RELATED APPLICATIONS

This is a continuation-in-part of U.S. application Ser. No. 08/713,407, filed on Sep. 13, 1996 now pending.

FIELD OF THE INVENTION

The present invention relates to surgical implements, and more particularly to a surgical handle assembly for receiving cutting tools of different shapes which are used in hair transplantation procedures.

BACKGROUND OF THE INVENTION

Many hair transplantation procedures have been developed for transferring hair and living hair follicles from a donor to a donee. For example, hollow cylindrical punches are commonly used to cut a small diameter hole in the scalp of a donee. Thereafter, a skin graft containing hair and follicles which has been removed from a donor is transplanted into a hole in the scalp of the donee. The size of the hole formed in the donee's scalp by the hollow punch controls the number of hairs which may be transplanted in a single hair transplant graft. Usually, only a small number of hairs, such as 2 to 6 hairs are transplanted in a single graft. Sometimes, only a single hair is transplanted.

Surgeons may also choose to use a blade to form a small incision in the donee's scalp which receives a skin graft. In addition, small sized holes in the donee's scalp for receiving skin grafts may be formed by a solid cylindrical punch or needle.

A typical hair transplant procedure requires a large number of grafts which must be obtained from a donor. In some instances, hair is removed from and transplanted to the same individual. Hair grafts may be obtained from a donor scalp by carefully removing sections of hair-laden scalp using either a scalpel or a multi-bladed knife. These sections of hair-laden scalp are divided into small skin grafts each having a small number of hairs.

Hair transplants are generally made by cutting either a small slit with a knife or a circular hole with a hollow or solid punch in the scalp of the donee and transplanting a graft containing a few hairs into the slit or hole in the scalp of the donee. Often, both slits formed by a knife and holes formed by a punch are used in the same transplantation procedure. For instance, a knife may be used to form slits in the hair line because the slits form a more natural hair line, while a combination of slits and holes may be used further back on the donee's head to provide a desired hair thickness.

Surgical implements which are conventionally used in hair transplantation procedures include a mini-blade scalpel, a cylindrical solid punch, or a cylindrical hollow punch. These surgical implements are also used in a variety of sizes. Therefore, in a single hair transplantation procedure, a surgeon may use knives, solid punches, and hollow punches of a variety of different sizes. Each of these known surgical implements has a base or non-cutting portion of a different size and shape. Thus, a different type of a handle is used for the different surgical implements. Therefore, a surgeon must keep on-hand handles of different types to accommodate the different types of surgical implements used in the transplantation procedure. In addition, the surgeon must continually get accustom to the feel of different handles when switching surgical implements during a surgical procedure.

SUMMARY OF THE INVENTION

The present invention provides a surgical handle for use in hair transplantation procedures which can accommodate each of the surgical implements commonly used in these hair transplantation procedures. The surgical handle can accommodate both a knife with flat blade and various cylindrical tubular punches.

According to one aspect of the present invention a surgical handle kit includes a plurality of surgical implements including at least one surgical knife blade, and at least one cylindrical surgical punch, a handle body including a distal end and a proximal end, a plurality of flexible chuck members formed at the distal end of the handle body for securing the knife and the cylindrical punch to the handle, an elongated slot defined by the plurality of flexible chuck members for receiving the surgical knife blade, and a cylindrical bore defined by the plurality of flexible chuck members for receiving the cylindrical punch.

According to a further aspect of the present invention a surgical handle includes a handle body including a distal end and a proximal end, a first elongated lengthwise slot in the distal end of the handle for receiving a substantially flat surgical implement, a cylindrical lengthwise bore in the distal end of the handle for receiving a cylindrical end of a surgical implement, and a chucking mechanism at the distal end of the knife handle which may be tightened to secure one of the surgical implement having the flat end and the surgical implement having the cylindrical end in place in the handle body.

According to the present invention a surgical handle includes a handle body including a distal end and a proximal end, a cylindrical lengthwise bore in the distal end of the handle for receiving a cylindrical end of a hollow surgical implement, a chucking mechanism at the distal end of the knife handle which may be tightened to secure the cylindrical end in place in the handle body, and a through hole in the handle communicating an exterior surface of the handle body with the cylindrical bore. The through hole being sufficiently large to enable tissue which has accumulated in the cylindrical bore to exit the handle body, and the through hole extending completely through the handle body.

According to an additional aspect of the present invention a method of performing a hair transplantation procedure with a surgical handle includes the steps of: providing a surgical handle which accommodates a plurality of surgical implements having base portions of different shapes, the surgical implements including surgical knife blades, cylindrical hollow punches, and cylindrical solid punches; selecting a first surgical implement and affixing the base portion of the first surgical implement in the surgical handle; performing a first surgical implantation procedure; removing the first surgical implement from the surgical handle; selecting a second surgical implement which has a base portion of a different shape from the first surgical implement and affixing the base portion of the second surgical implement in the surgical handle; and performing a first surgical implantation procedure.

BRIEF DESCRIPTION OF THE DRAWING FIGURES

The invention will be described in greater with reference to the accompanying drawings in which like elements bear like reference numerals, and wherein.

DETAILED DESCRIPTION OF THE PREFERRED EMBODIMENTS

Figure 1:
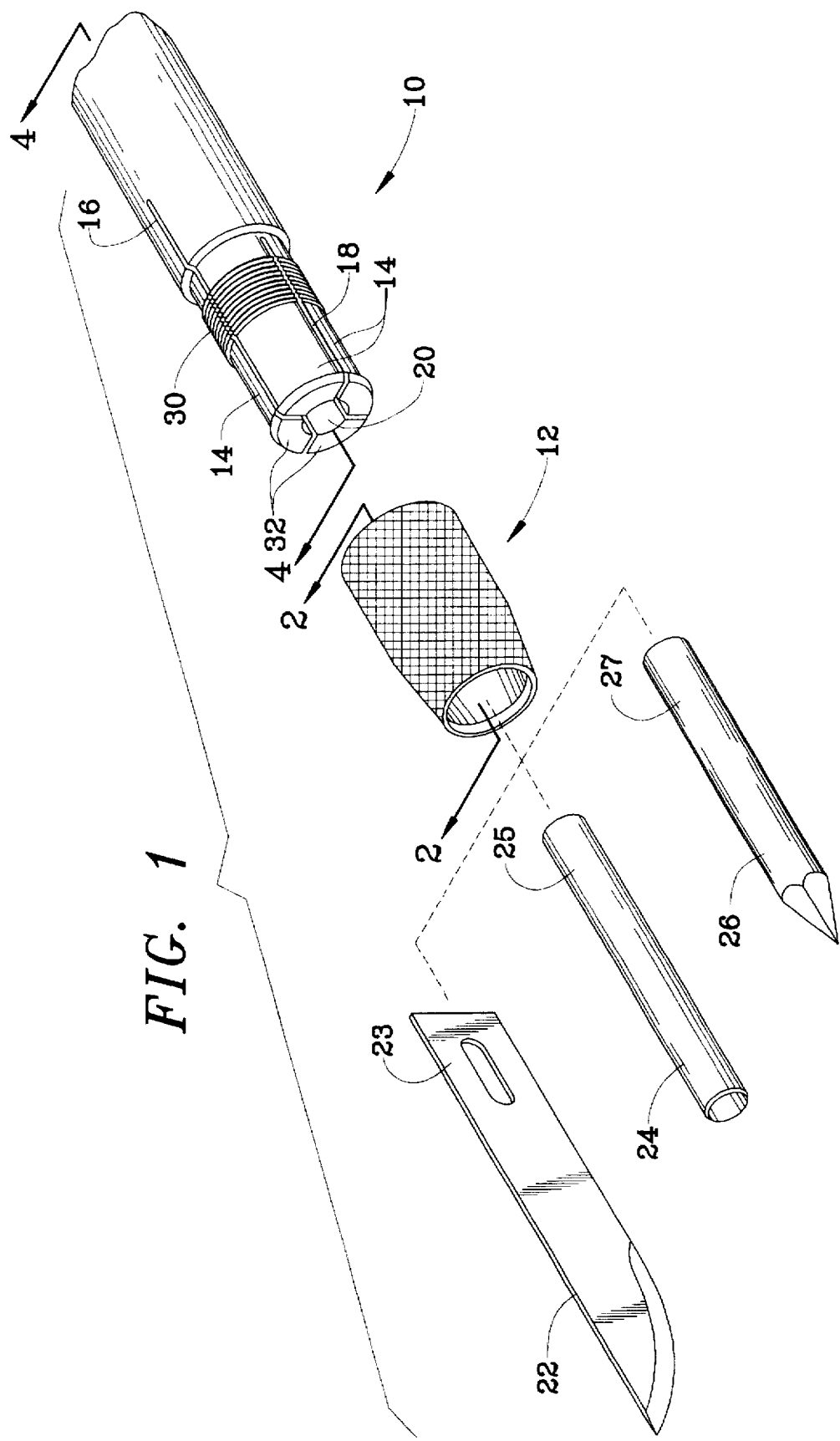
FIG. 1 is an exploded perspective view of a surgical handle and associated surgical implements according to one embodiment of the present invention.

FIG. 1 is an exploded view of the handle and implements which are received in the handle according to the present invention. The handle includes a handle body 10 and a sleeve 12 threaded onto a distal end of the handle body. A distal end of the handle body includes four flexible chuck members 14 arranged to form a substantially cylindrical distal end. The flexible chuck members 14 define a first longer slot 16, a second shorter slot 18 and a cylindrical center bore 20.

The surgical implements which are received in the handle body 10 according to the present invention include a flat surgical blade 22, a cylindrical hollow punch 24, and a cylindrical solid punch 26. The term cylindrical punch as used herein is intended to include hollow punches, solid punches, and needles. As illustrated in FIG. 1, the base portions 23, 25, 27 of the surgical implements which are received in the handle body 10 are of different shapes. For example, the end or base portion 23 of the flat surgical blade 22 is rectangular, while the base portions or ends 25, 27 of the cylindrical punches 24, 26 are cylindrical in shape. The surgical implements which are illustrated in FIG. 1 are shown by way of example only and not limitation. Surgical implements of many different known configurations can also be used with the handle according to the present invention.

The first longer slot 16 of the handle body 10 is configured to receive the base portion 23 of the flat surgical blade 22. The first longer slot 16 is substantially perpendicular to the second shorter slot 18 and has a greater length than the second shorter slot. The cylindrical center bore 20 is configured to receive a cylindrical base portion of a surgical implement such as the cylindrical base portions 25, 27 of the cylindrical hollow punch 24 or the cylindrical solid punch 26. The cylindrical center bore 20 is formed by curved inner surfaces of each of the flexible chuck members 14.

Figure 4:
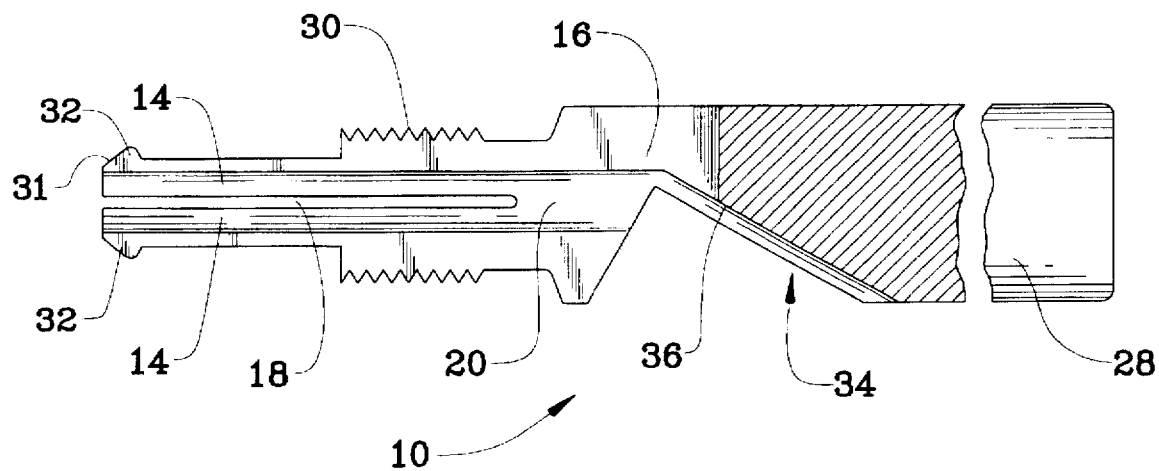
FIG. 4 is a cross-sectional side view of the body of the surgical handle taken along the line 4—4 of FIG. 1.

The handle body 10 is illustrated in more detail in FIG. 4. The cross-sectional side view of FIG. 4 is taken along the center of the handle body 10 through the first longer slot 16 of the handle body. As illustrated in FIG. 4, the handle body 10 includes a handle portion 28 for grasping by the surgeon. The handle portion 28 may be knurled or otherwise textured to facilitate griping by the surgeon. The handle body 10 also includes a threaded portion 30 for receiving the sleeve 12. The threads of the threaded portion 30 are located on the exterior surfaces of the flexible chuck members 14.

As illustrated in FIG. 4, the flexible chuck members 14 each include an enlarged portion 32 formed at a distal end thereof. The enlarged portions 32 of the flexible chuck members 14 act as chucking surfaces which engage a portion of the sleeve 12 and causes the flexible chuck members 14 to flex inwardly to firmly engage and secure the surgical implement which is held by the handle.

Figure 2:
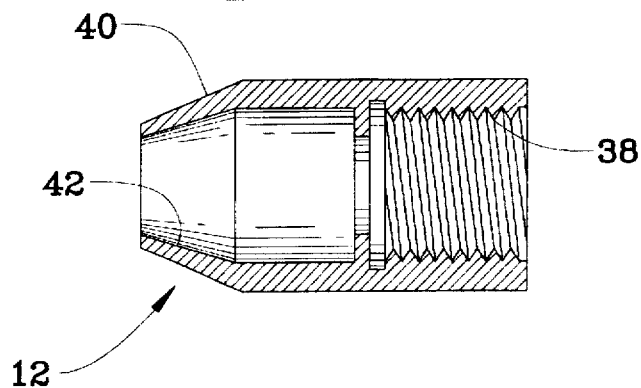
FIG. 2 is a cross-sectional side view of an exemplary sleeve of a surgical handle according to one embodiment of the present invention.
Figure 3:
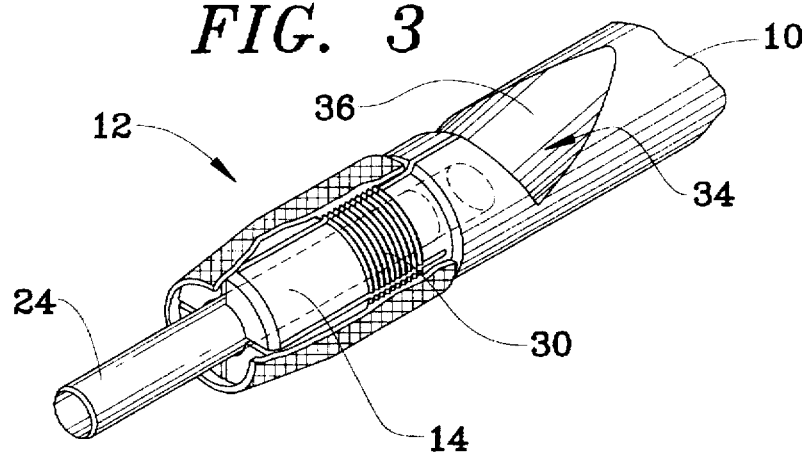
FIG. 3 is a perspective view of a surgical handle according to one embodiment of the present invention with the sleeve partially sectioned.

As illustrated in FIGS. 3 & 4, the handle body 10 of the surgical handle according to one embodiment of the present invention also includes a notch 34 which extends from an exterior surface of the handle portion 28 to the cylindrical center bore 20 of the handle body. The notch 34 is formed across an entire side surface of the handle portion 28 approximately perpendicular to the plane of the longer slot 16. The notch 34 communicates the cylindrical center bore 20 with the exterior of the handle. Thus, the notch 34 allows a plug of tissue which is removed by a hollow surgical implement such as the cylindrical hollow punch 24 to pass through the hollow punch, through the center bore 20, and exit the handle through the notch 34. As depicted in FIG. 3, the lower surface 36 of the notch 34 is preferably concave in shape to provide a smooth surface for exiting plugs of tissue to traverse when exiting the center bore 20. The exemplary sleeve 12 as illustrated in the cross-sectional side view of FIG. 2 includes an internal threaded section 38 which is received over and engages the external threads of the threaded portion 30 on the handle body 10. The sleeve 12 also includes a tapered distal portion 40 which is in the form of a conical shape having an internal cam surface 42. The internal cam surface 42 of the sleeve engages the external cam surfaces 31 on the enlarged portions 32 of the flexible chuck members 14. When the sleeve 12 is threaded onto the handle body until the internal cam surface 42 of the sleeve engage the external cam surfaces 31 of the flexible chuck members 14, the sleeve may be further tightened so that the flexible chuck members are flexed inwardly. The inward flexing of the flexible chuck members 14 frictionally secures a surgical implement firmly in place in the handle body 10.

FIG. 3 illustrates a cylindrical hollow punch 24 secured to the surgical handle 10 according to an exemplary embodiment of the present invention. The internal threaded portion 38 of the sleeve 12 is attached to the threaded portion 30 of the handle body 10 such that the internal cam surface 42 of the tightened sleeve engages the external cam surface 31 of the enlarged portions 32 of the flexible chuck members 14. Thus, the cylindrical hollow punch 24 is frictionally held in place by the inward pressure of the four flexible chuck members 14.

In operation, the surgeon may place a first surgical implement such as the flat surgical blade 22 of FIG. 1 within the handle body 10 with a flat portion of the blade extending through the first longer slot 16 of the handle body. The surgeon then tightens the sleeve 12 by rotating the sleeve on the handle body 10 to flex the flexible chuck members 14 inwardly and secure the surgical blade 22 firmly in place in the handle. When the surgeon wishes to use a different surgical implement, such as, a cylindrical punch, the flat surgical blade 22 is removed and either the cylindrical hollow punch 24 or the cylindrical solid punch 26 is inserted into the cylindrical center bore 20 of the handle body 10. Once a cylindrical punch is located within the cylindrical bore 20, the surgeon again tightens the sleeve 12 by rotating the sleeve with respect to the handle body 10 to press the flexible chuck members 14 against the shaft of the cylindrical punch. In this manner, the surgeon can easily switch from one surgical implement to another irrespective of the shape of the base of the surgical implement.

The use of a single handle 10 which can accommodate surgical implements of different shapes improves the surgeon's efficiency and reduces the total number of surgical tools needed to perform a transplantation procedure. In addition, the use of a handle 10 having the same configuration with a plurality of different implements allows the surgeon to use different implements without having to get accustom to different handles each time a different implement is used. The reduced number of surgical tools also simplifies cleanup.

The flat surgical blades 22 and cylindrical hollow and solid punches 24, 26 for use in the present invention are generally known to surgeons in the hair transplantation field. These knives and punches come in a variety of standard sizes and are generally formed of stainless steel. These implements may be sterilizable, reusable implements or may be disposable, single-use implements. Other configuration surgical implements may also be used with the handle according to the present invention. For example, the tip of a hollow punch may be elliptical, square, or triangular. Furthermore, the cylindrical lengthwise bore of the handle body may receive different shaped ends of various surgical implements, such as an elliptical end of an elliptical hollow punch. The handle body 10 and sleeve 12 are preferably formed of a sterilizable material such as stainless steel. However, the handle body 10 and sleeve 12, may also be disposable in which case they may be formed of non-sterilizable materials such as plastic.

The hollow cylindrical punch 24 may alternatively be conically shaped such that the diameter of the punch increases from the punch tip to the end received by the handle body 10. This configuration is particularly useful because plugs of tissue traveling through the punch will have less of a tendency to catch on the interior wall of the punch. Thus, the conically shaped hollow punch permits tissue plugs to easily exit the punch.

The longer slot 16 in the handle is preferably sized for receiving a known type of flat surgical blade 22 called a mini-blade. The longer slot 16 can be on the order of about 2.0 mm to 5.0 mm, preferably 3.0 mm to 4.0 mm, more preferably about 3.5 mm in width. A slot 16 having a width of about 3.5 mm and length of between 1.0 mm and 3.0 mm will accommodate a conventional mini-blade which is used in transplantation procedures. The slot 16 can also be sized to receive a known type of larger flat surgical blade called a scalpel blade, which is typically wider than a mini-blade.

The cylindrical center bore 20 of the handle 10 which accommodates the hollow or solid punches 24, 26 can have a diameter of about 2.0 mm to about 5.0 mm, preferably about 3.2 mm. A center bore of 3.2 mm will accommodate punches having diameters between 1.0 mm and 3.0 mm. In an alternative embodiment of the present invention, the notch 34 may be eliminated and the cylindrical center bore 20 may extend through the length of the handle. The overall length of the handle body 10 can be between about 30 mm and 100 mm, preferably about 50 mm. The foregoing dimensions have been included by way of example and not limitation.

Figure 5:
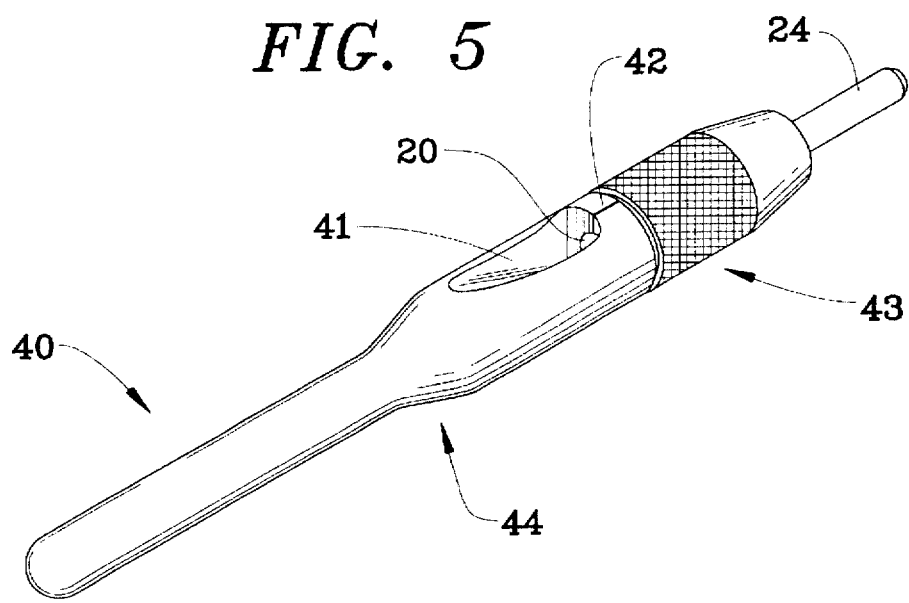
FIG. 5 is a perspective view of an alternative embodiment of the surgical handle according to the present invention.

FIG. 5 illustrates the surgical handle 40 according to an alternative embodiment of the present invention. The handle 40 has an elongated notch 41, similar in function to the notch 34 of the knife 10 illustrated in FIG. 3. However, the elongated notch 41 illustrated in FIG. 5 is more elongated than the notch 34 of FIG. 3. The elongated notch 41 smoothly communicates the center bore with the exterior surface of the handle 40, and guides plugs of tissue exiting the center bore 20. Since the notch 41 is elongated, plugs of tissue which are removed by the hollow surgical implement 24 easily exit the center bore 20 and the notch. This elongated configuration provides less of an initial angle which plugs of tissue must encounter when initially existing the center bore 20. The elongated notch 41 is preferably about 20 mm long and 5 mm wide, and may be made from an end mill by procedures known in the art.

Figure 6:
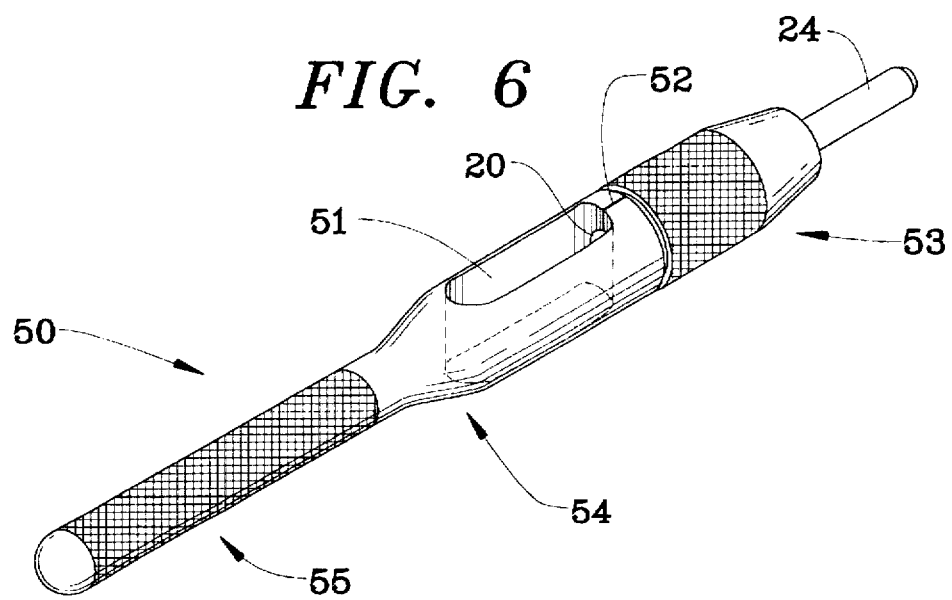
FIG. 6 is a perspective view of another alternative embodiment of the surgical handle according to the present invention.

FIG. 6 illustrates another embodiment of the surgical handle 50 according to the present invention. The surgical handle 50 shown in FIG. 6 includes an elongated radially extending through hole 51. The elongated through hole 51 is preferably elongated and runs or extends completely through the handle 50. Each end of the through hole 51 is preferably curved such that there are no sharp edges on which exiting plugs of tissue may catch. Since the through hole 51 passes completely through the body of the handle 50, there are two openings through which the plugs of tissue may exit the handle. This configuration of the through hole 51 easily permits the plugs of tissue to exit the handle 50 with the assistance of gravity. The through hole 51 is sufficiently large to enable tissue which has accumulated in the cylindrical bore to exit the handle body 50. In the embodiment of the handle 50 illustrated in FIG. 6, the longitudinal axis passing through the hole 51 is preferably perpendicular with the longitudinal axis of the center bore 20. The through hole is preferably about 20 mm long and 5 mm wide.

Both surgical handles 40 and 50 of FIGS. 5 and 6 include an extended first longer slot 42, 52. The extended first longer slots 42, 52 are longer than the first longer slot 16 of the embodiment of the present invention illustrated in FIG. 1. More specifically, the extended first longer slots 42, 52 are preferably at least 7 mm in length such that each may accommodate longer blades than the first longer slot 16 if the embodiment depicted in FIG. 1. Likewise, the sleeves 43, 53 are elongated to accommodate this increase in length and to easily adapt to a surgeon's grip.

The exemplary surgical handles 40, 50 illustrated in FIGS. 5 and 6 are also shaped differently than the handle illustrated in FIG. 1. The handles 40, 50 include a taper 44, 54 which improves the forward balance of the handles. Furthermore, the taper 44, 54 lessens the weight of the surgical handles, which assists the surgeon in performing numerous surgical operations with the handle, and enables the surgeon to easily grip and maneuver the handle during surgical operations.

The alternative shape of the handles 40, 50 is formed by the tapers 44, 54. The handles 40, 50 can be designed so that the taper preferably begins to slope inwardly towards the handle at approximately 30 mm from the tips of the flexible chuck members. The taper 44, 54 can then end approximately 5 mm from where they start. The length of each handle 40, 50 is preferably about 100 mm and has a first cross sectional diameter before the taper begins, and a second cross sectional diameter after the taper ends. The first diameter can be on the order of approximately 7.9 mm and tapers down to the second diameter which can be on the order of approximately 6.35 mm. The foregoing dimensions have been included by way of example and not limitation.

The handles 50, 60 of the embodiment illustrated in FIGS. 5 and 6 may also include a knurled surface 55 for assisting the surgeon in gripping the handle.

Figure 7:
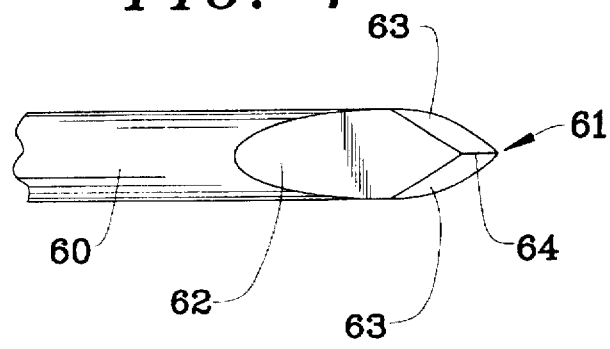
FIG. 7 is a perspective view of an alternative embodiment of a surgical implement for use with a surgical handle according to the present invention.

FIG. 7 illustrates an alternative embodiment of a preferred surgical implement. The surgical implement illustrated in FIG. 7 is an exemplary cylindrical solid punch 60 used to make slit incisions. The cylindrical solid punch 60 includes a solid body similar to a conventional needle, but also includes an edge 64 and a spear point 61. The edge 64 and spear point 61 are formed by grinding three surfaces of the needle. First, the large flat surface 62 is ground at a shallow angle, and then the smaller surfaces 63 are ground at a steeper angle. The surfaces 63 intersect with the outer cylindrical surface of the punch 60. The surfaces 63 intersect with each other to form the edge 64. The edge 64 intersects with the outer cylindrical surface to form the spear point 61. Surface 62 acts to define the beginning of the edge 64 farthest from the spear point 61. This configuration is particularly easy to manufacture and maintain sharp. A surgeon may resharpen the cylindrical solid punch simply by grinding the surfaces 62 and 63 in the above-described manner. This configuration surgical implements is much simpler and results in a finer point than previous cylindrical solid punch needles. The cylindrical solid punch 60 may be fashioned from wire needles that are well known in the art. For example, the cylindrical solid punch 60 can be made from a 20 gauge or 18 gauge wire needle.

Figure 8:
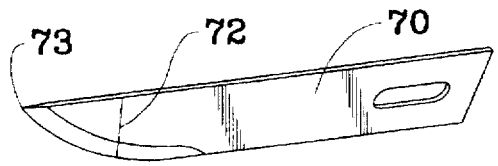
FIG. 8 is a perspective view of a second alternative embodiment of a surgical implement for use with a surgical handle according to the present invention.

FIG. 8 illustrates a surgical implement for use with the surgical handle. The exemplary surgical implement is a surgical knife blade 70 having a mark 72 located thereon. The mark 72 is located at a predetermined distance from the tip 73 of the knife 70. This predetermined distance corresponds to the desired penetration depth of the surgical implement. When performing surgical procedures with the surgical handle, it is desirable to estimate and control the surgical implement penetration depth. Thus, the mark 72 provides the surgeon with the necessary reference point by which to estimate and control the penetration depth of the surgical implement, which in the embodiment illustrated in FIG. 8, is the surgical blade 70.

The mark 72 is located between 4 and 6 mm, preferably 5 mm from the surgical implement tip. Thus, the mark 72 assists the surgeon from over or under penetrating the scalp of a patient. The mark 72 may be formed by any variety of methods well known in the art. For example, the mark 72 may be painted, anodized, etched, scratched, molded, or burnt on the surface of the knife 70. Furthermore, the mark 72 may be formed on any variety of surgical implements that may be used with the present invention, such as the punches described above. The mark may also be a different color than that of the surgical implement.

The mark 72 may also be formed on other surgical implements such as forceps commonly used during hair transplantation procedures. Forceps used in hair transplantation procedures typically are shaped like tongs or pincers and are used for grasping, manipulating, or extracting hair grafts and donor strips. Forceps with a mark 72 located near the tips of the forceps are particularly useful because the surgeon may control the penetration depth of the tips by visually tracking the distance between the mark and the surface of penetration.

While the invention has been described in detail with reference to a specific embodiment thereof, it will be apparent to one skilled in the art that various changes and modification can be made, and equivalents employed, without departing from the spirit and scope of the invention as defined in the claims.

What is claimed is:

1. A surgical handle kit comprising:

a plurality of surgical implements including at least one surgical knife blade, and at least one cylindrical surgical punch;

a handle body including a distal end and a proximal end;

a plurality of flexible chuck members formed at the distal end of the handle body for securing the knife and the cylindrical punch to the handle;

an elongated slot defined by the plurality of flexible chuck members for receiving the surgical knife blade; and a cylindrical bore defined by the plurality of flexible chuck members for receiving the cylindrical punch.

2. The surgical handle kit according to claim 1, wherein the plurality of surgical implements include a plurality of cylindrical surgical punches including at least one hollow surgical punch for cutting plugs of tissue and at least one solid surgical punch.

3. The surgical handle kit according to claim 2, wherein the solid surgical punch is cylindrical and includes a plurality of intersecting flat surfaces defining an edge and a spear point.

4. The surgical handle kit according to claim 1, wherein the plurality of surgical implements includes a mark located at a predetermined distance from a tip of the implement, the predetermined distance corresponding to a desired penetration depth.

5. The surgical handle kit according to claim 1, wherein the plurality of flexible chuck members each include external threaded portions and cam surfaces, and including a sleeve having internal threads for being threaded onto the external threaded portions of the flexible chuck members to tighten the flexible chuck members about the surgical implements.

6. The surgical handle kit according to claim 1, wherein the handle body includes a side notch communicating an exterior surface of the handle body with the cylindrical bore.

* * * * *